United States Patent
Kasai et al.

(10) Patent No.: US 8,430,654 B2
(45) Date of Patent: *Apr. 30, 2013

(54) TUBING MISLOAD DETECTION MECHANISM FOR AN INFUSION PUMP

(75) Inventors: Takashi Kasai, Tokyo (JP); Kenji Honda, Tokyo (JP)

(73) Assignee: Namiki Seimitsu Houseki Kabushiki Kaisha (JP)

( * ) Notice: Subject to any disclaimer, the term of this patent is extended or adjusted under 35 U.S.C. 154(b) by 916 days.

This patent is subject to a terminal disclaimer.

(21) Appl. No.: 12/112,126

(22) Filed: Apr. 30, 2008

(65) Prior Publication Data

US 2009/0274567 A1 Nov. 5, 2009

(51) Int. Cl.
*F04B 43/08* (2006.01)

(52) U.S. Cl.
USPC .......................................................... 417/474

(58) Field of Classification Search ..... 417/474–477.14; 604/153
See application file for complete search history.

(56) References Cited

U.S. PATENT DOCUMENTS

| | | | |
|---|---|---|---|
| 5,090,877 A * | 2/1992 | D'Silva | 417/474 |
| 5,120,096 A * | 6/1992 | D'Silva | 292/241 |
| 6,629,955 B2 * | 10/2003 | Morris et al. | 604/153 |

FOREIGN PATENT DOCUMENTS

| | | |
|---|---|---|
| JP | 515589 | 1/1993 |
| JP | 5-277183 | 10/1993 |

* cited by examiner

*Primary Examiner* — Peter J Bertheaud
*Assistant Examiner* — Dnyanesh Kasture
(74) *Attorney, Agent, or Firm* — Studebaker & Brackett PC; Donald R. Studebaker

(57) ABSTRACT

A an infusion tube misfitting detection device for an infusion pump, which can be implemented at a low cost while maintaining safety. When a door unit is to be closed with respect to a pump body in a misloaded state of an infusion tube, a mislead detection inner door is pressed by the infusion tube to operate on a handle lock part provided to a handle. Accordingly, a claw portion of the handle lock part is pushed up, so that the door unit cannot be locked with the pump body 10 by inserting the claw portion into a rectangular through-hole 11*c* of a base plate. Therefore, the misloaded state can be identified.

6 Claims, 8 Drawing Sheets (a)

(b)

(a)　　　　　(b)

(a)

(b)

TUBING MISLOAD DETECTION MECHANISM FOR AN INFUSION PUMP

TECHNICAL FIELD

The present invention relates to a system for preventing misload of an infusion tube in an infusion pump having a door which is used for a medical intravenous apparatus or the like.

BACKGROUND

Conventionally, a peristaltic infusion pump is mainly used as a medical infusion pump for feeding a medicinal solution or the like in an infusion tube, in which a door is openably and closably provided to an infusion pump body having a pump mechanism.

The peristaltic infusion pump has a structure for performing feed, in which a plurality of fingers provided to a pump body perform reciprocating motion with individual phases to be in a peristaltic movement as a whole, so that infusion tubes disposed between the fingers and a receiving plate provided to the door are sequentially pressed toward a downstream so as to perform the feed. An example of the peristaltic infusion pump is disclosed in Japanese Patent Application Publication No. S-277183.

In such an infusion pump, if the infusion tube is not fitted at a correct position, when a door provided to the infusion pump is closed so as to perform infusion, an amount of a fed solution is greatly reduced, or any amount of the solution is not fed. Therefore, an infusion pump having a function of detecting a misloaded state of the infusion tube to prevent the misload of the infusion tube is desired.

As an example of an infusion pump having a function of preventing misload of the infusion tube, a technique of detecting the misload of the tube by using a position detection sensor such as a pressure sensitive sensor to control an alarm about abnormal fitting is disclosed in Patent Document 2.

According to the function of preventing misload of the infusion tube in the infusion pump disclosed in Japanese Patent Application Publication No. S-15589, the misfit state of the infusion tube is correctly detected, and the alarm is issued based on the detection, so that the misfit state can be speedily released for a proper and prompt response. Therefore, the infusion pump has a good safety as a medical instrument.

According to a conventional method of detecting misload of an infusion tube by using a position detection sensor, the sensor may be expensive, an output of the sensor needs to be adjusted, or software for electrical control needs to be developed. Therefore, the infusion pump may become expensive.

In order to implement an inexpensive infusion pump maintaining safety, it is preferable to provide a means for detecting misload of an infusion tube.

In order to solve the problems, the present invention according to claim 1 provides a tubing misload detection mechanism for an infusion pump comprising a door, an inner door, and an interlocking part.

The door is supported with a shaft by a pump body of the infusion pump in an openable/closable state; the inner door is supported with a shaft by the door; and when the infusion tube fitted in the pump body presses the inner door, the inner door is moved due to the pressing of the infusion tube.

In the tubing misload detection mechanism for an infusion pump, the interlocking part operates in interlock with the inner door, so that the door is prevented from being stably held in the pump body.

In the tubing misload detection mechanism for an infusion pump, the interlocking part is disposed to a handle provided to the door in the tubing misload detection mechanism for an infusion pump.

The door can be locked with the pump body by inserting a claw portion provided to the interlocking part into a through-hole provided to the pump body.

In the tubing misload detection mechanism for an infusion pump, when the interlocking part operates in interlock with the movement of the inner door, the claw portion of the interlocking part is moved, so that the door is prevented from being stably held in the pump body.

In the tubing misload detection mechanism for an infusion pump, the interlocking part is disposed inside the door in the tubing misload detection mechanism for an infusion pump.

The interlocking part has a prismatic-column-shaped or circular-column-shaped protrusion portion, the protrusion portion is disposed inside the door, and the interlocking part operates in interlock with the movement of the inner door.

In the tubing misload detection mechanism for an infusion pump, the protrusion portion protrudes to an outside of the door and to a position in a pivotable range where the operation of the handle provided to the door is prevented, so that the door is prevented from being stably held in the pump body.

According to the invention, when the infusion tube is misloaded, a manipulator can visually identify the state that the door is not entirely closed, so that the misloaded state of the infusion tube can be detected.

Since the misloaded state of the infusion tube can be detected by using a mechanical structure without use of an electrical position detection sensor, the misloading of the infusion tube can be detected irrespective of abnormality of sensitivity of a sensor due to a use environment or electrical problems such as disconnection of electrical wire lines.

Since conventional expensive sensor or electrical circuits are not needed, a task or facility for adjusting sensitivity of sensor in a production process for the infusion pump is not needed, so that it is possible to implement a tubing mislead detection mechanism for an infusion pump at a low cost with a safety maintained.

Further, since a force exerted from an inner door can be directly exerted on the interlocking part, it is possible to implement a tubing mislead detection mechanism for an infusion pump with a simple structure.

In addition to implementation of the mislead detection mechanism at a low cost, a protrusion portion which is provided to a position where the operation of the handle is prevented is suitable. Therefore, the invention can be applied to any types of handles including handles having various shapes or handles having no lock mechanism.

Hereinafter, tubing misload detection mechanisms for an infusion pumps according to preferred embodiments of the present invention will be described with reference to the accompanying drawings. In the embodiments, the same elements are denoted by the same reference numerals.

FIRST EMBODIMENT

In a tube misload detection mechanism according to a first embodiment of the present invention, a door cannot be locked with a pump body in a closed state thereof when an infusion tube is not loaded at a correct position in the pump body, so that a misloaded state of the infusion tube can be detected.

More specifically, when the door is to be closed in a state that the infusion tube is not correctly loaded to a groove of the pump body, the infusion tube presses an inner door provided to the door, so that a force due to the pressing is transferred to a claw-shaped part that enables the door to be locked with the pump body. Therefore, the claw-shaped part is moved to a position where the door cannot be locked to be held in a stable state.

Hereinafter, structures and functions of a tube misload detection mechanism and an infusion pump using the tube misload detection mechanism according to the embodiment will be described in detail.

[Infusion Pump]

Figure 1:
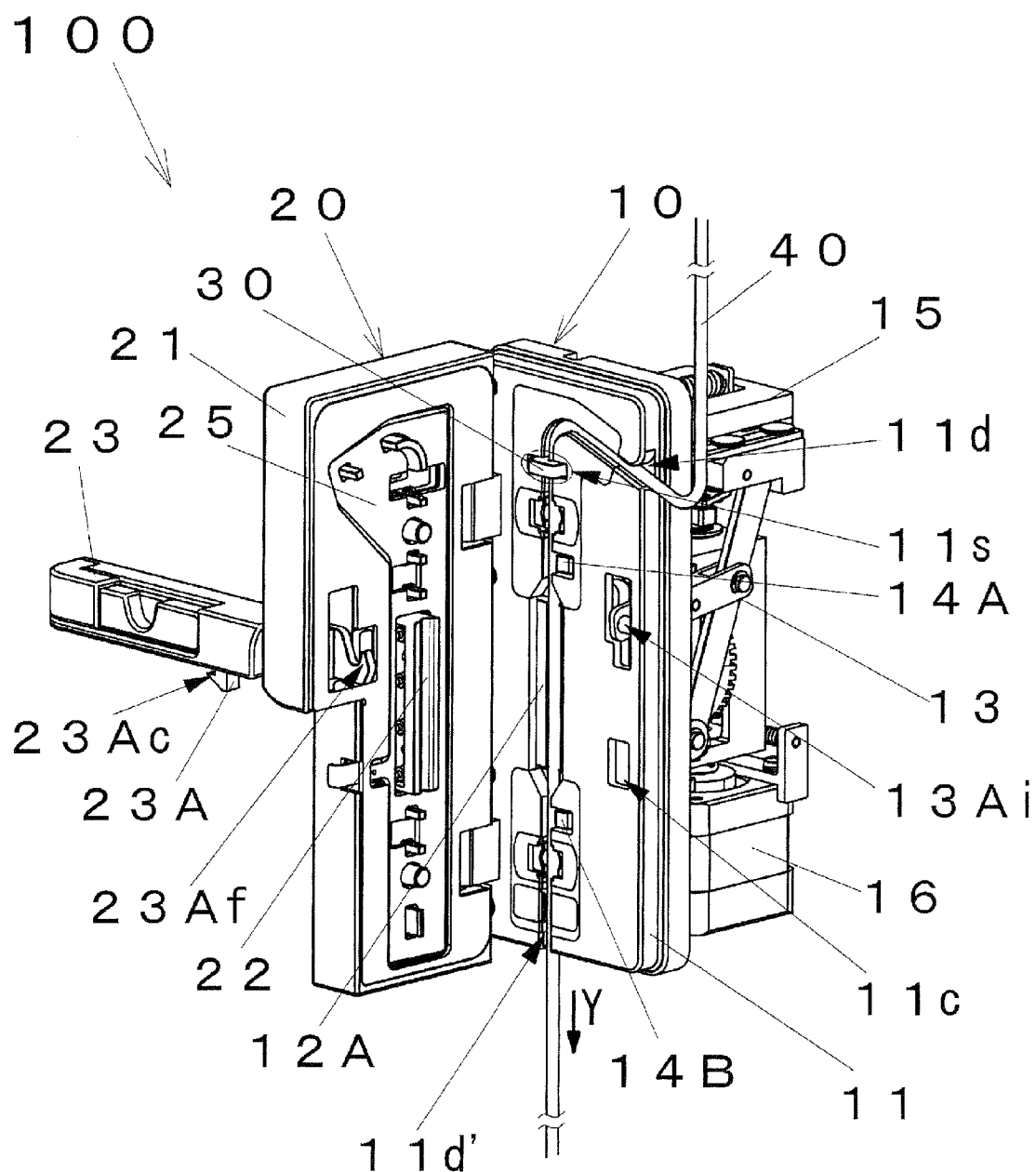
FIG. 1 is a perspective view illustrating an infusion pump having a tube misload detection mechanism according to an embodiment of the present invention.

FIG. 1 is a perspective view illustrating an infusion pump 100 having the tube misload detection mechanism according to the first embodiment of the present invention. The infusion pump 100 is mainly constructed with a pump body 10 and a door unit 20 which is openably and closably provided to the pump body 10. In FIG. 1, the door unit 20 is in an opened state.

The pump body 10 is mainly constructed with a valve mechanism part having a valve 14A and a valve 14B, a slide clamp mechanism part 15, an interlock mechanism part 13, a shuttle mechanism part having a V-grooved driving part 12A, and a motor 16, which are disposed on a base plate 11.

The door unit 20 is mainly constructed with a handle 23 provided to a door part 21, a V-grooved fixing part 22, and a misload detection inner door 25.

The infusion tube 40 is loaded in the pump body 10 in a state that the infusion tube is closed by a slide clamp 30 which is a clamp member for the infusion tube.

As shown in FIG. 1, the infusion tube 40 closed by the slide clamp 30 is loaded at the correct position in a state that a portion of the slide clamp 30 is mounted on a slide clamp mounting portion 11s of the base plate 11 and the other portions are mounted on the groove portion 11d-11d'.

Figure 2:
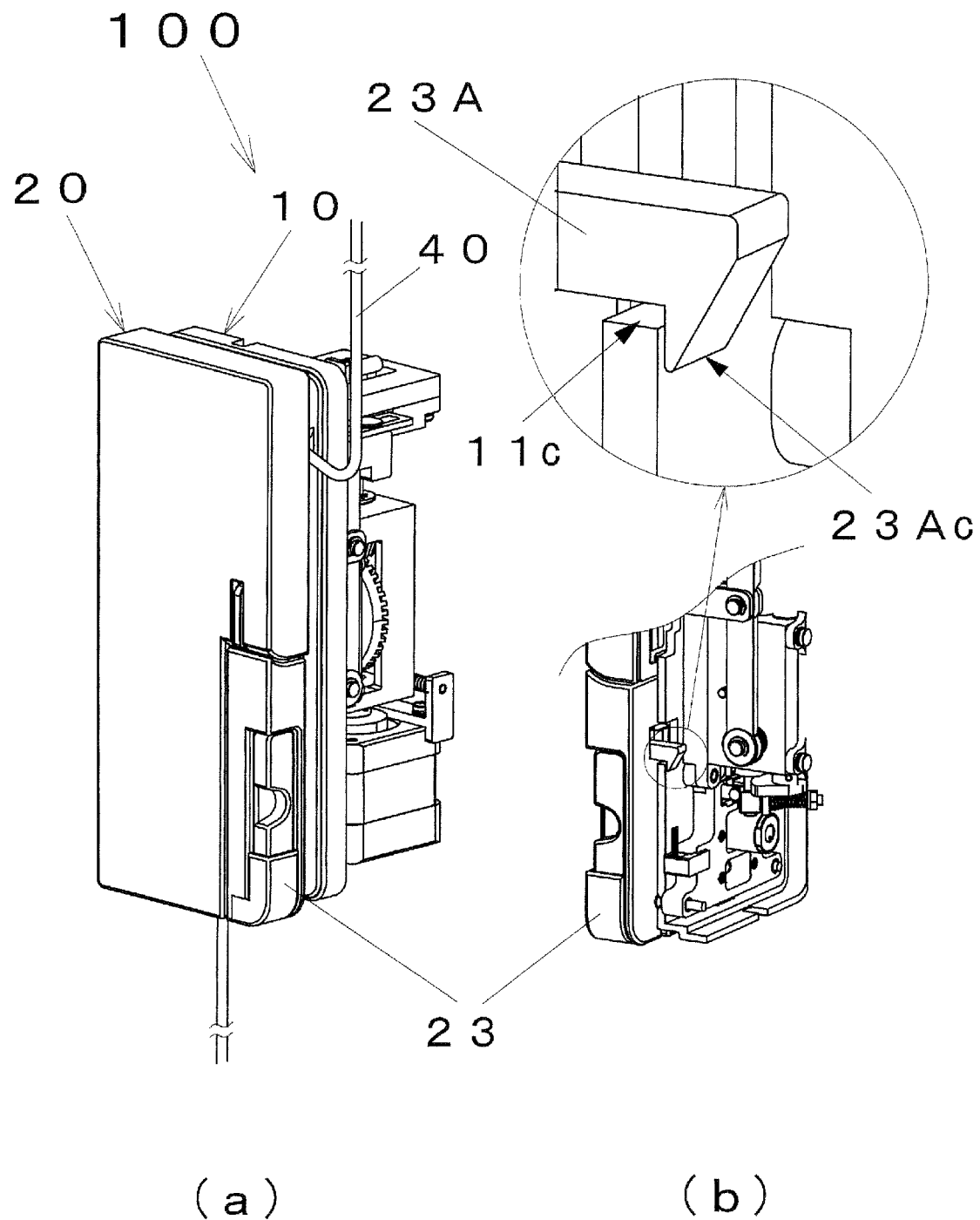
FIGS. 2(a) and (b) are views illustrating a state that the infusion pump according to the embodiment of the present invention is correctly loaded in a pump body.

FIG. 2 (a) illustrates a state that the door unit 20 is entirely closed with respect to the pump body 10 after the infusion tube is loaded at the correct position in the pump body.

As shown in FIG. 2 (b), in the state that the door unit 20 is entirely closed with respect to the pump body 10, a claw portion 23Ac of a handle lock part 23A provided to the handle 23 is inserted into a rectangular through-hole 11c of the base plate 11 so as to be locked with the pump body 10.

In the state shown in FIG. 2 (a) that the infusion tube 40 is loaded at the correct position and the door unit is closed, the infusion pump 100 feeds a solution by allowing the V-grooved driving part 12A to perform reciprocating motion in a direction perpendicular to the feeding direction and in a direction parallel to the V-grooved fixing part 22 opposite thereto so that the V-grooved fixing part 22 may repetitively press the infusion tube.

According to the tube misload detection mechanism of the embodiment, when the infusion tube 40 is not fitted at the correct position in the pump body 10, the door unit 20 cannot be locked with the pump body 10 in the closed state thereof, so that the infusion pump 100 can be prevented from being used in the misloaded state of the infusion tube 40.

[Tube Mislead Detection Mechanism]

Figure 3:
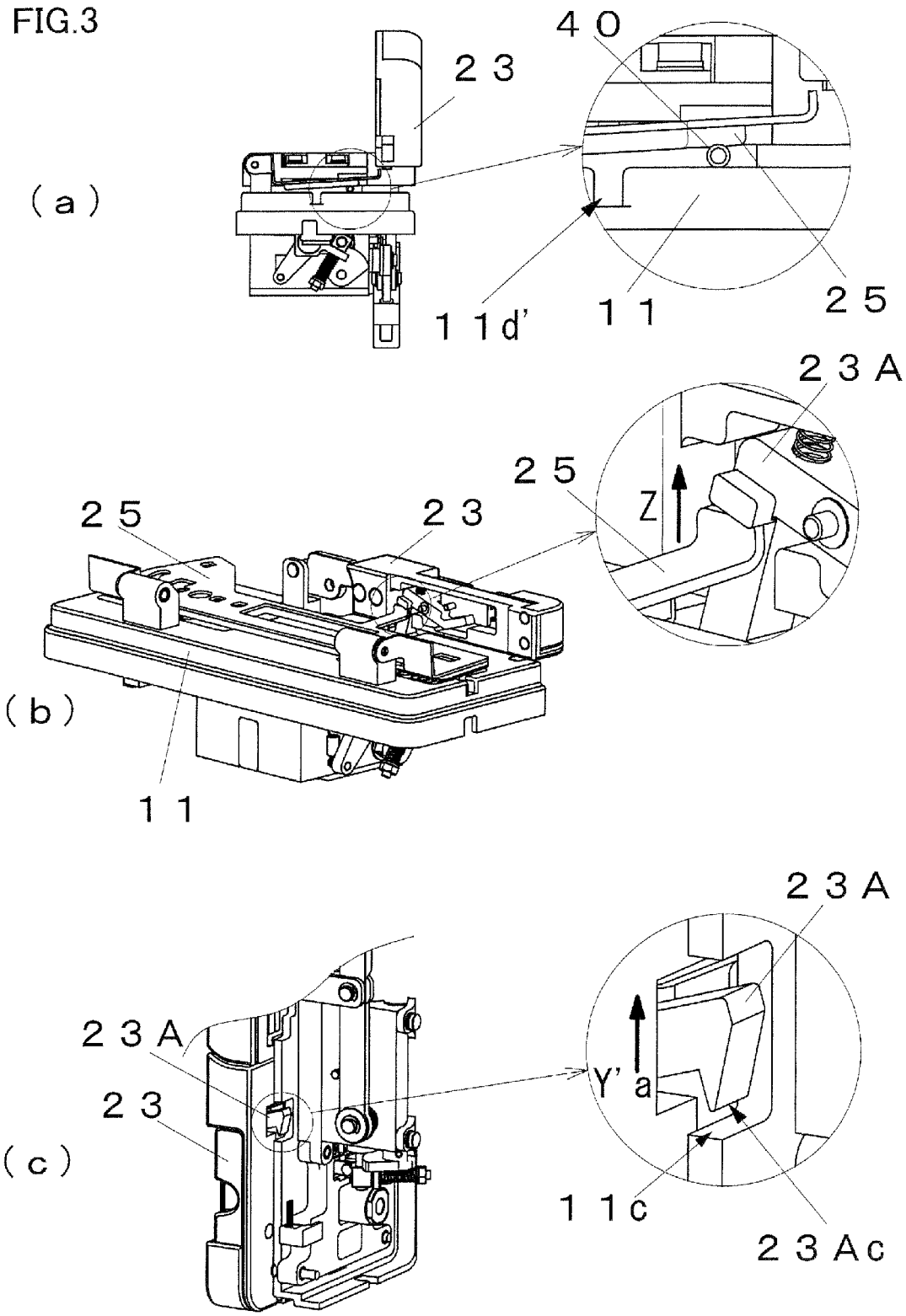
FIGS. 3 (a), (b) and (c) are views illustrating a state that the infusion pump according to the embodiment of the present invention is not correctly loaded in the pump body.

FIG. 3 (a) is a bottom view of the infusion pump 100 illustrating a state that the infusion tube 40 is misloaded in the infusion pump 100.

When the infusion tube 40 is fitted correctly, the infusion tube passes by the groove portion 11d' of the base plate 11. However, as shown in FIG. 3 (a), when the infusion tube is not correctly loaded, the infusion tube 40 is interposed between a portion excluding the groove portion 11d-11d' of the base plate 11 and the mislead detection inner door 25.

In this case, the mislead detection inner door 25 is pressed by the infusion tube 40, so that a force is exerted to a handle lock part 23A provided to the handle 23 in the Z direction (see FIG. 3 (b)).

Accordingly, a position of the claw portion 23Ac of a handle lock part 23A is moved in the Y' a direction, and the claw portion 23Ac is inserted into a rectangular through-hole 11c of the base plate 11, so that the door unit 20 cannot be locked with the pump body 10 (see FIG. 3 (c)).

When the door unit 20 is to be closed with respect to the pump body 10 in the state that the door unit 20 is not locked with the pump body 10, a hook portion 23Af of the handle 23 is hooked with a portion 13Ai of the pump body, or the door unit is in a half-opened state. Therefore, a user can identify the misloaded state.

Second Embodiment

In a tube misload detection mechanism according to a second embodiment of the present invention, a protrusion portion for preventing manipulation of a handle in interlock with pressing of an inner door by the infusion tube when the infusion tube is not fitted at a correct position in a pump body is provided, so that a misloaded state of the infusion tube can be detected.

Hereinafter, a latching method of a door in an infusion pump using a structure of the tube misload detection mechanism according to the embodiment and detailed structure and function of the tube mislead detection mechanism will be described.

[Infusion Pump]

Figure 4:
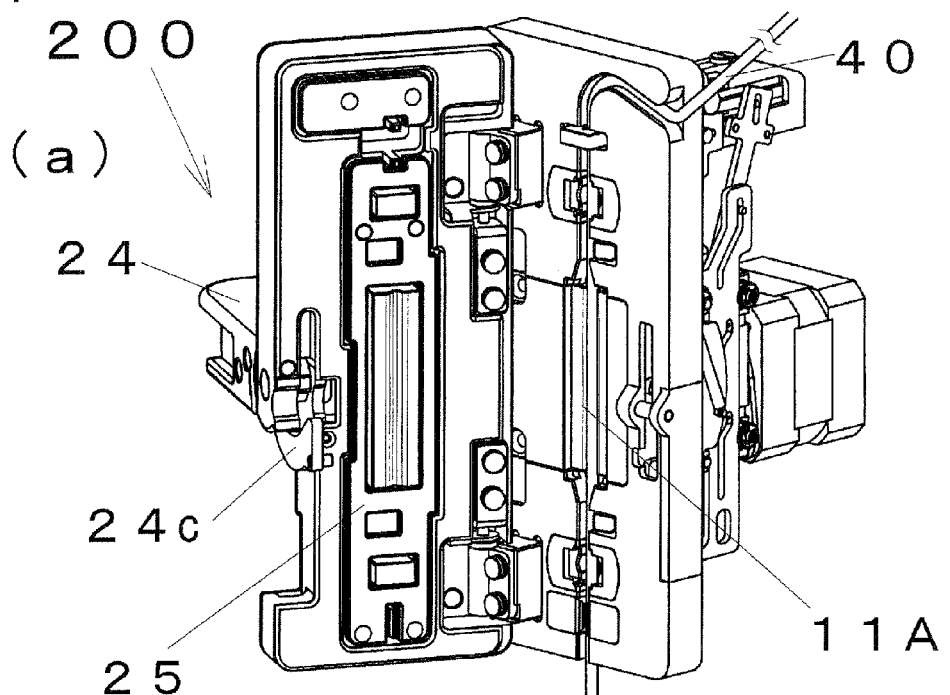
FIGS. 4 (a) and (b) are perspective views illustrating an infusion pump having a tube misload detection mechanism according to another embodiment of the present invention.
Figure 4:
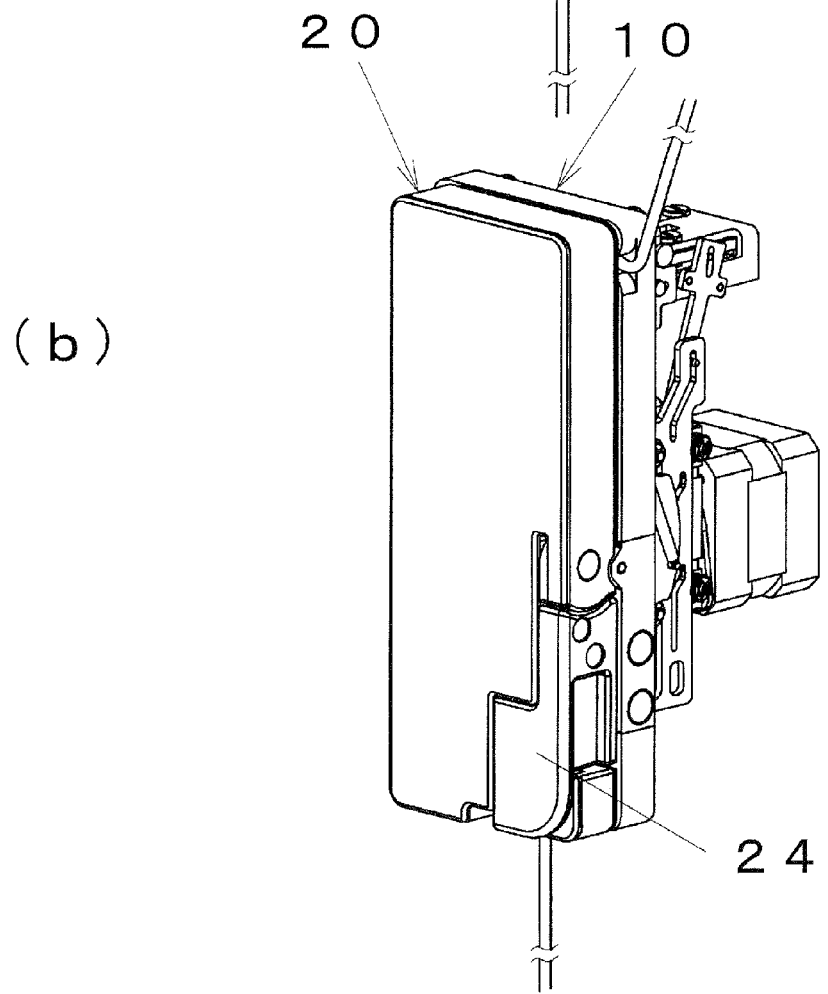

FIG. 4 is a perspective view illustrating an infusion pump 200 having the tube mislead detection mechanism according to the second embodiment of the present invention. The infusion pump 200 is mainly constructed with a pump body 10 and a door unit 20 which is openably and closably provided to the pump body 10. In FIG. 4 (a), the door unit 20 is in an opened state.

A basic construction of the infusion pump 200 is the same as that of the infusion pump 100 according to the first embodiment. When the infusion tube is misloaded, the misload detection inner door is pressed so that mechanisms in the door unit 20 are operated. However, in the infusion pump 200, the handle 24 has no handle lock part having a claw portion, and the door unit 20 is locked with the pump body 10 in a different method.

When an infusion tube 40 is fitted at a correct position in the pump body 10, a curved arm portion 24c of the handle 24 is stably in contact with a latch roller 11A provided to a base plate 11 to be inserted into the door unit 20, so that the door unit 20 in the closed state is locked with the pump body 10 to be held in a stable state (see FIG. 4 (*b*)).

[Tube Misload Detection Mechanism]

Figure 5:
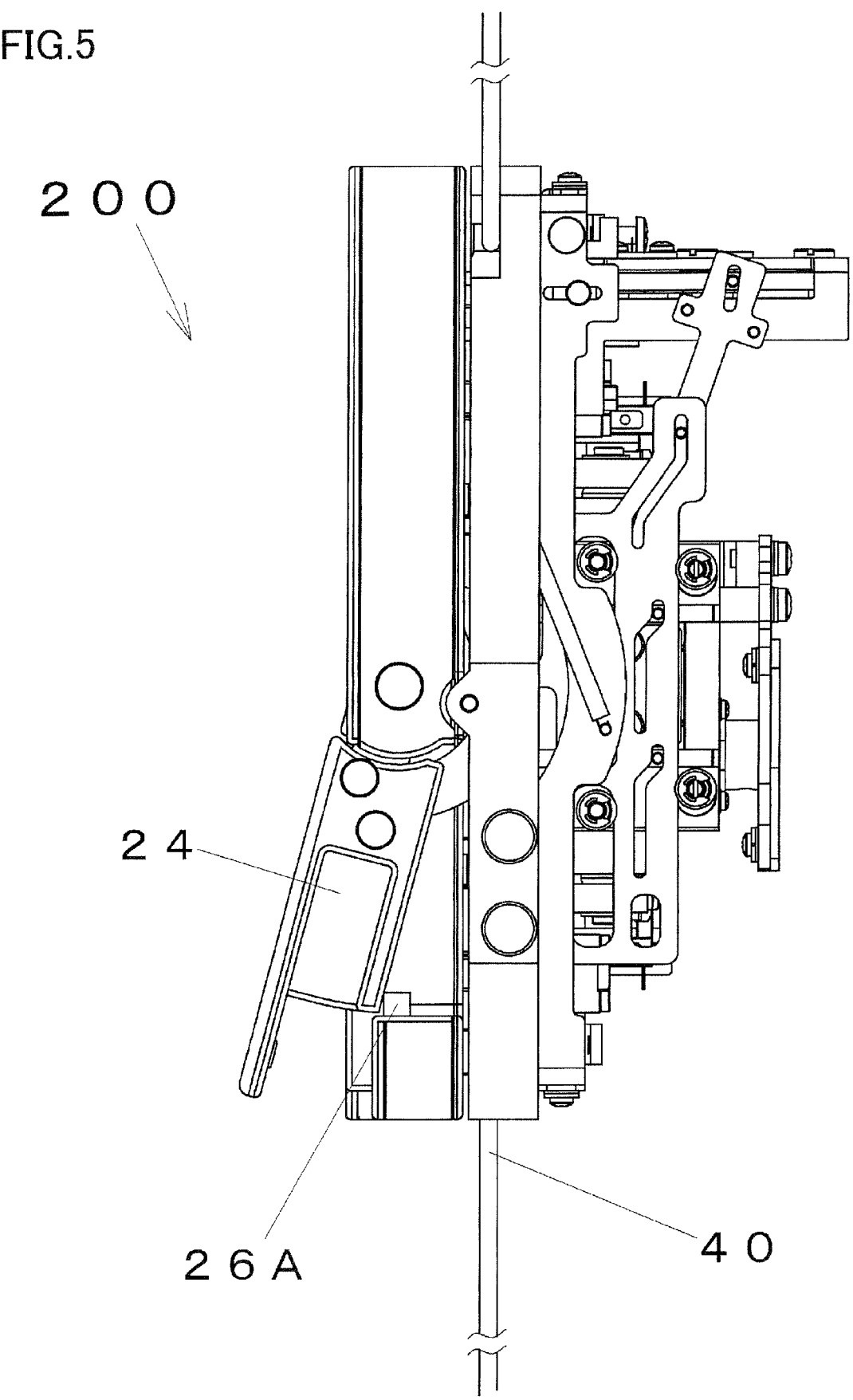
FIG. 5 is a view illustrating a state that the infusion pump according to the embodiment of the present invention is not correctly fitted in the pump body.

FIG. 5 is a view illustrating a misloaded state of the infusion tube 40 in the infusion pump 200. In this case, the mislead detection inner door 25 (see FIG. 4 (*a*)) is pressed by the infusion tube 40, and accordingly, a stopper 26A is protruded, so that manipulation of the handle 24 is prevented.

Figure 6:
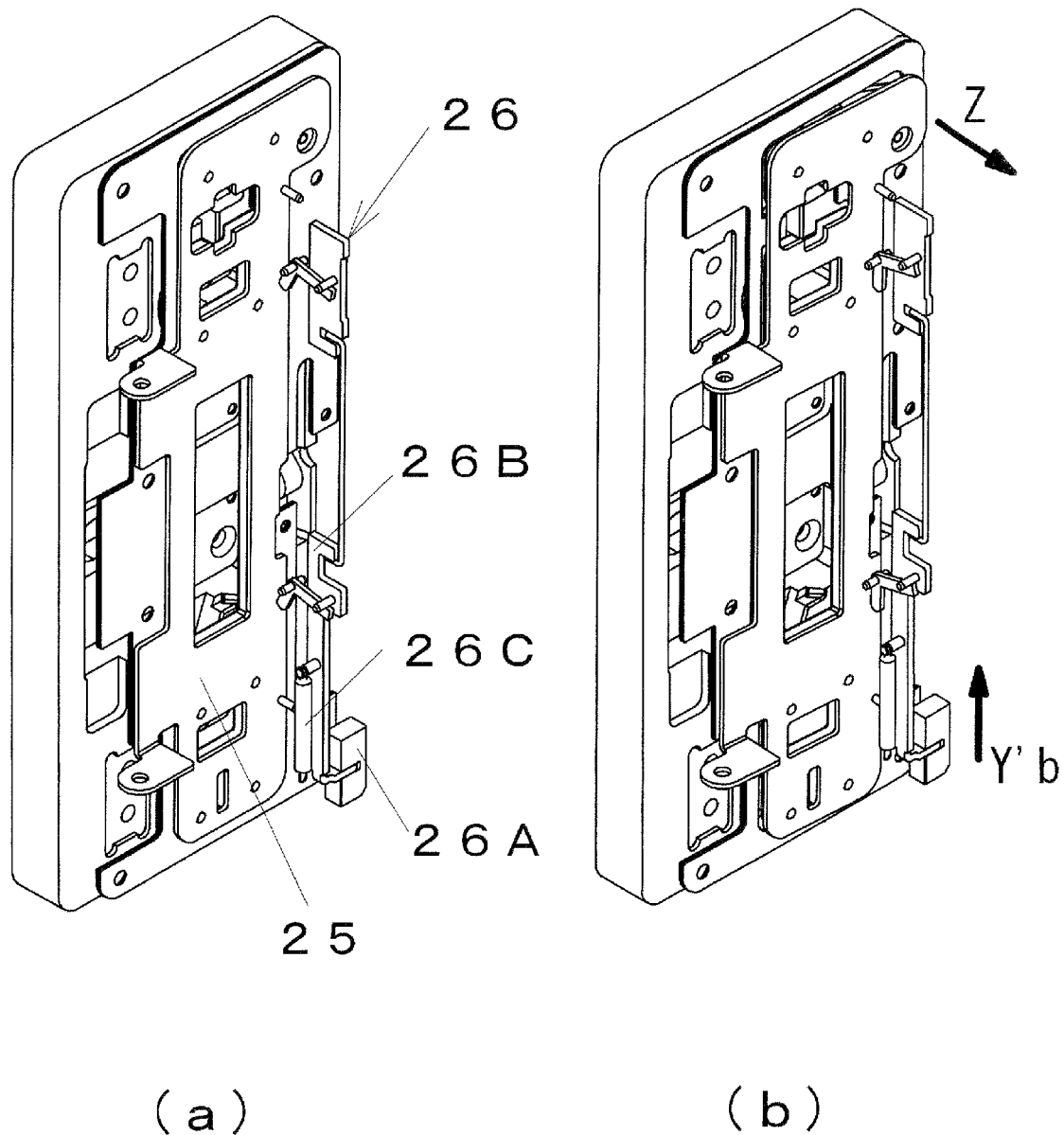
FIGS. 6 (a) and (b) are views illustrating a structure of a tube misload detection mechanism according to another embodiment of the present invention.

FIG. 6 is a view illustrating a structure of a stopper mechanism 26 which is cooperatively operated with the misload detection inner door 25. The stopper mechanism is constructed with a stopper 26A, a stopper holder 26B, and a stopper spring 26C.

FIG. 6 (*a*) is a view illustrating a state of the stopper mechanism 26 when the misload detection inner door 25 is not pressed by the infusion tube 40 due to misloading of the infusion tube 40 at a correct position.

In this case, a stopper spring 26C of which one end is held by the door part presses a stopper holder 26B provided integrally with a prismatic-column-shaped stopper 26A downwards.

FIG. 6 (*b*) is a view illustrating a state of the stopper mechanism 26 when the misload detection inner door 25 is pressed by the infusion tube 40 in the Z direction due to misload of the infusion tube 40.

In this case, as shown in FIG. 5, the misload detection inner door 25 presses the stopper holder 26B provided integrally with the stopper 26A in the Y'b direction so as to protrude the stopper 26A, so that manipulation of the handle 24 can be prevented.

In the embodiment, the prismatic-column-shaped stopper 26A is used. However, a circular-column-shaped stopper can also be used as a suitable protrusion portion for preventing manipulation of the handle 24.

Third Embodiment

In a tube misload detection mechanism according to a third embodiment of the present invention, a position of a part of locking a door is moved in interlock with pressing of an inner door by an infusion tube when the infusion tube is not misloaded at a correct position in a pump body, so that the part of locking the door cannot be locked with the door. Therefore, a misloaded state of the infusion tube can be detected.

Hereinafter, a latching method of a door in an infusion pump using a structure of the tube misload detection mechanism according to the embodiment and structure and function of the tube misload detection mechanism will be described.

Figure 7:
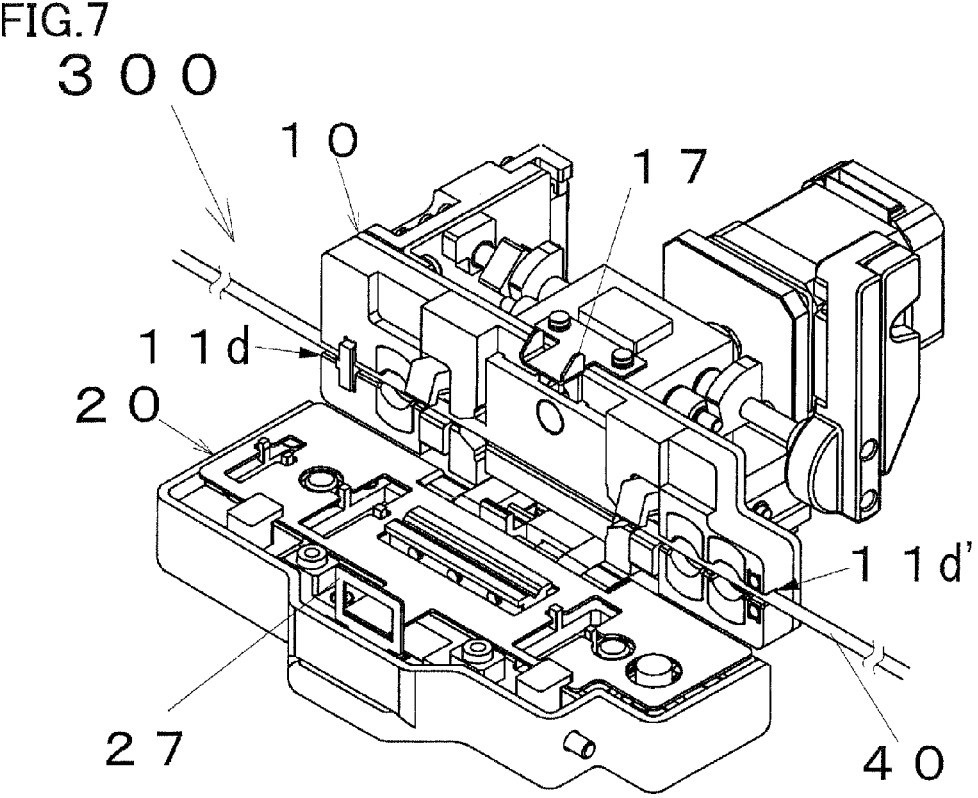
FIGS. 7 (a) and (b) are perspective views illustrating an infusion pump having a tube misload detection mechanism according to another embodiment of the present invention.
Figure 7:
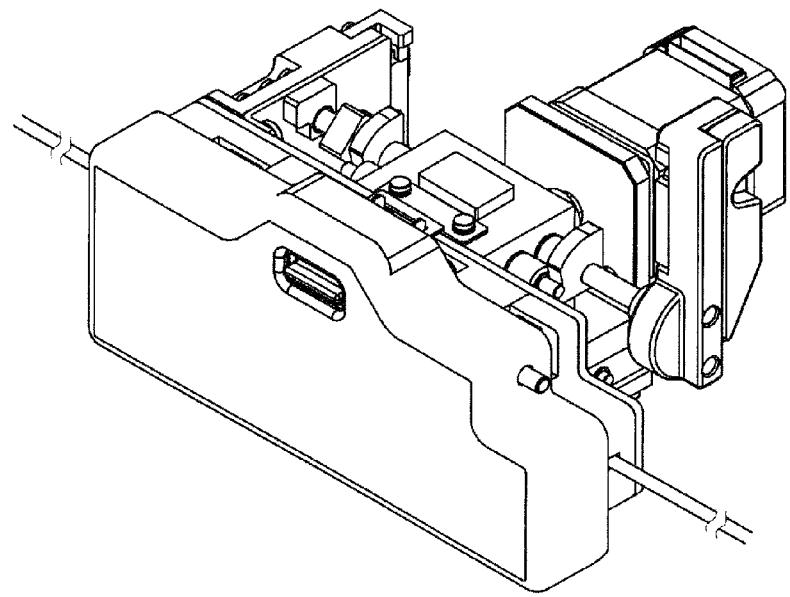

FIG. 7 (*a*) is a perspective view illustrating an infusion pump 300 having the tube misload detection mechanism according to the third embodiment of the present invention. The infusion pump 300 is mainly constructed with a pump body 10 and a door unit 20 which is openably and closably provided to the pump body 10. In FIG. 7 (*a*), the door unit 20 is in the opened state.

When the infusion tube 40 is fitted at a correct position in the pump body 10, a door lock part 27 is latched with a lock part 17 of the pump body, so that the door unit 20 can be locked with the pump body 10 in the closed state thereof (see FIG. 7 (*b*)).

Figure 8:
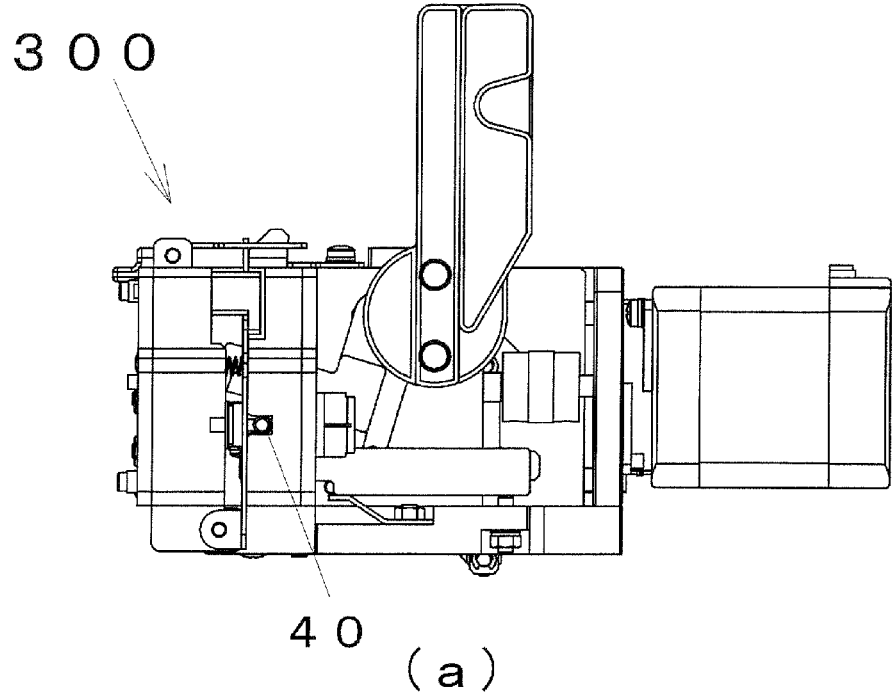
FIGS. 8 (a) and (b) are views illustrating a state that the infusion pump according to the embodiment of the present invention is correctly loaded in the pump body and a state that the infusion pump is not correctly loaded.
Figure 8:
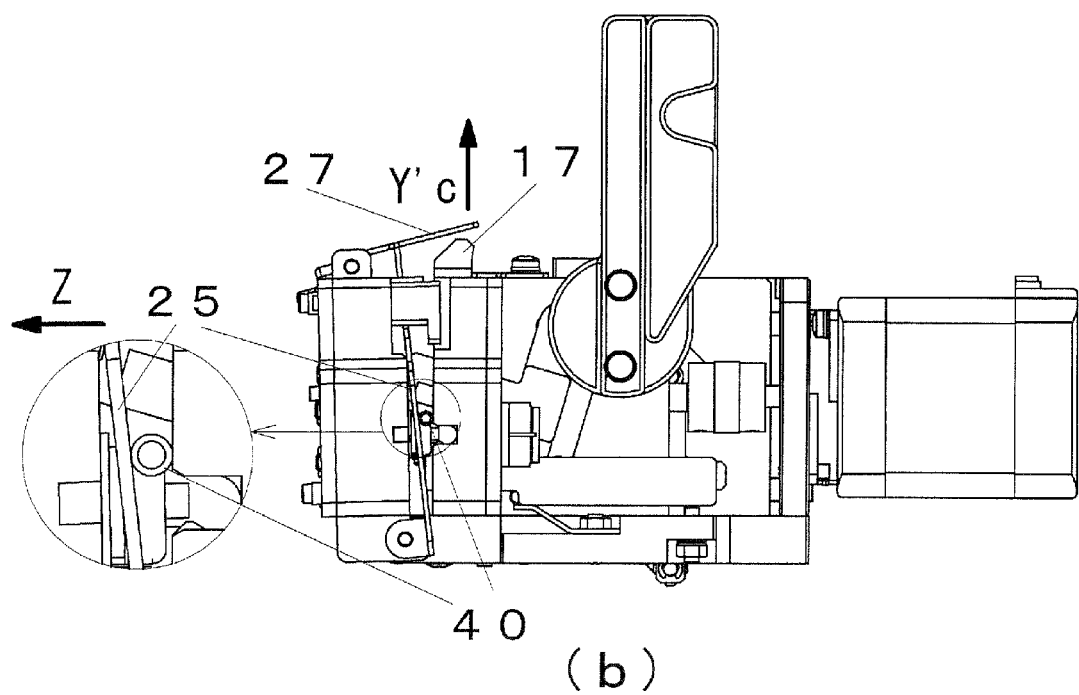

FIG. 8 (*a*) illustrates a state that the infusion tube 40 is fitted at a correct position in the pump body 10, so that the door unit 20 is closed with respect to the pump body 10. In this case, sine the infusion tube 40 is correctly inserted into the groove portion 11d-11d' of the base plate 11, the infusion tube 40 cannot press the misload detection inner door 25.

FIG. 8 (*b*) illustrates a state that the infusion tube 40 is not correctly inserted into the groove portion 11d-11d' of the base plate 11 but misloaded. In this case, the infusion tube 40 presses the mislead detection inner door 25 in the Z direction, and the door lock part 27 is moved in the Y'c direction in interlock with the pressing, so that the door unit 20 cannot be closed with respect to the pump body 10.

Hereinbefore, embodiments of the infusion pump according to the present invention are described, but various modifications may be implemented without departing from the scope of the present invention.

For example, the feeding mechanism is not limited to the shuttle type, but the tube misload detection mechanism according to the present invention can be applied to any types of infusion pumps that have a door and a handle to feed a solution in an infusion tube in a closed state of the door as well as a peristaltic type.

The invention claimed is:

1. A tubing misload detection mechanism for an infusion pump having a pump body, comprising:
    a door hingely connected to the pump body of the infusion pump,
    a misload-detection inner door hingely connected to the door, and
    an interlocking part,
    wherein a hinge axis of said door and said inner door are in a same longitudinal direction and the inner door is positioned between the door and the pump body when the door is in a closed position with the pump body, and
    wherein, when a misloaded infusion tube fitted in the pump body presses against the inner door, the inner door is moved due to the pressing of the infusion tube, and the interlocking part operates in conjunction with the position of the inner door thus preventing the door from being latched and completely shut with the pump body.

2. The tubing misload detection mechanism for an infusion pump according to claim 1,
    wherein the interlocking part is disposed on a handle provided on the door,
    wherein a claw portion provided to the interlocking part is inserted into a through-hole portion provided to the pump body, so that the door is lockable with the pump body when the infusion tube is not misloaded, and
    wherein, when the interlocking part operates in interlock with movement of the inner door, the claw portion of the interlocking part is moved, so that the door is prevented from being latched and fully shut on the pump body.

3. The tubing misload detection mechanism for an infusion pump according to claim 2, further comprising:
    wherein when the infusion tube is misloaded and in an improper position between the pump body and the misload-detection inner door, a gap is created by the infusion tube between the door and the pump body and thus preventing the claw portion of the interlocking part from reaching and latching onto the through-hole portion on the pump body to fully close the door.

4. The tubing misload detection mechanism for an infusion pump according to claim 1, wherein the interlocking part is disposed inside the door,
wherein the interlocking part has a prismatic-column-shaped or a circular-column-shaped protrusion portion,
wherein the protrusion portion is disposed inside the door, and
wherein, when the interlocking part operates in interlock with movement of the inner door, the protrusion portion protrudes to an outside of the door and to a position in a range where the pivot of the handle provided to the door is prevented, so that the door is prevented from being stably held in the pump body.

5. The tubing misload detection mechanism for an infusion pump according to claim 1, wherein the hinge axis of said door and the hinge axis of said inner door are co-linear.

6. The tubing misload detection mechanism for an infusion pump according to claim 1, wherein said door and said inner door are hingely connected to a same shaft.

* * * * *